United States Patent
Wasserman (10) Patent No.: US 11,883,652 B2
(45) Date of Patent: Jan. 30, 2024

(54) OPTIMIZATION OF COMPOSITE ELECTRODE

(71) Applicant: Novocure GmbH, Root (CH)

(72) Inventor: Yoram Wasserman, Haifa (IL)

(73) Assignee: Novocure GmbH, Root (CH)

( * ) Notice: Subject to any disclaimer, the term of this patent is extended or adjusted under 35 U.S.C. 154(b) by 21 days.

(21) Appl. No.: 17/550,423

(22) Filed: Dec. 14, 2021

(65) Prior Publication Data

US 2022/0193404 A1 Jun. 23, 2022

Related U.S. Application Data

(60) Provisional application No. 63/128,265, filed on Dec. 21, 2020.

(51) Int. Cl.
*A61N 1/32* (2006.01)
*A61N 1/20* (2006.01)
*A61B 18/14* (2006.01)

(52) U.S. Cl.
CPC ............ *A61N 1/326* (2013.01); *A61N 1/205* (2013.01); *A61B 2018/147* (2013.01)

(58) Field of Classification Search
CPC ...... A61N 1/326; A61N 1/205; A61N 1/0456; A61N 1/36002; A61N 1/3603; A61N 1/0476; A61B 2018/147
See application file for complete search history.

(56) References Cited

U.S. PATENT DOCUMENTS

| | | | |
|---|---|---|---|
| 2015/0335898 A1* | 11/2015 | Carlson | A61N 1/0551 607/59 |
| 2017/0281934 A1 | 10/2017 | Biladi et al. | |
| 2018/0050200 A1* | 2/2018 | Wasserman | A61K 41/0052 |
| 2020/0155835 A1* | 5/2020 | Wasserman | A61N 1/08 |
| 2020/0269043 A1 | 8/2020 | Wasserman et al. | |

OTHER PUBLICATIONS

International Search Report and Written Opinion (PCT/IB2021/061711), dated Mar. 14, 2022, 13 pages.

* cited by examiner

*Primary Examiner* — Mallika D Fairchild
(74) *Attorney, Agent, or Firm* — DUNLAP CODDING, P.C.

(57) ABSTRACT

Apparatus and methods for imposing electric fields through a target region in a body of a patient are described. The apparatus includes a sensor array having a plurality of temperature sensors with a plurality of first temperature sensors of the sensor array connected to a first conductor, and a plurality of second temperature sensors connected to a second conductor. A circuit is configured to provide a known amount of electricity via the first conductor and the second conductor to a third temperature sensor, the third temperature sensor within the plurality of first temperature sensors, and within the plurality of second temperature sensors.

20 Claims, 5 Drawing Sheets

OPTIMIZATION OF COMPOSITE ELECTRODE

CROSS REFERENCE TO RELATED APPLICATIONS/INCORPORATION BY REFERENCE STATEMENT

The present patent application claims priority to the provisional application identified by U.S. Ser. No. 63/128,265, filed on Dec. 21, 2020, the entire content of which is hereby incorporated herein by reference.

STATEMENT REGARDING FEDERALLY SPONSORED RESEARCH OR DEVELOPMENT

Not Applicable.

BACKGROUND

Tumor Treating Fields (TTFields or TTFs) are low intensity (e.g., 1-3 V/cm) alternating electric fields within the intermediate frequency range (50 kHz to 1 MHz) that target solid tumors by disrupting mitosis. This non-invasive treatment targets solid tumors and is described, for example, in U.S. Pat. Nos. 7,016,725; 7,089,054; 7,333,852; 7,565,205; 8,244,345; 8,715,203; 8,764,675; 10,188,851; and 10,441,776. TTFields are typically delivered through two pairs of transducer arrays that generate perpendicular fields within the treated tumor; the transducer arrays that make up each of these pairs are positioned on opposite sides of the body part that is being treated. More specifically, for the OPTUNE® system, one pair of electrodes of the transducer arrays is located to the left and right (LR) of the tumor, and the other pair of electrodes is located anterior and posterior (AP) to the tumor. TTFields are approved for the treatment of glioblastoma multiforme (GBM), and may be delivered, for example, via the OPTUNE® system (Novocure Limited, St. Helier, Jersey), which includes transducer arrays placed on the patient's shaved head.

Each transducer array used for the delivery of TTFields in the OPTUNE® device comprises a set of non-conductive ceramic disk electrodes, which are coupled to the patient's skin (such as, but not limited to, the patient's shaved head for treatment of GBM) through a layer of conductive medical gel. To form the ceramic disk electrodes, a conductive layer is formed on a top surface of nonconductive ceramic material. A bottom surface of the nonconductive ceramic material is coupled to the conductive medical gel. The nonconductive ceramic material is a safety feature to ensure that direct-current signals are blocked from unintentionally being transmitted to the patient by mistake. By interposing a nonconductive ceramic material between the conductive layer and the conductive medical gel, the prior art system was thought to ensure the patient remains protected. The purpose of the medical gel is to deform to match the body's contours and to provide good electrical contact between the arrays and the skin; as such, the gel interface bridges the skin and reduces interference. The device is intended to be continuously worn by the patient for 2-4 days before removal for hygienic care and re-shaving (if necessary), followed by reapplication with a new set of arrays. As such, the medical gel remains in substantially continuous contact with an area of the patient's skin for a period of 2-4 days at a time, and there is only a brief period of time in which the area of skin is uncovered and exposed to the environment before more medical gel is applied thereto.

One approach to applying the TTField in different directions is to apply the field between a first set of electrodes for a period of time, then applying a field between a second set of electrodes for a period of time, then repeating that cycle for an extended duration (e.g., over a period of days or weeks).

In order to generate the TTFields, current is applied to each electrode of the transducer array. The application of current over a period of time causes each electrode to warm and eventually become hot, and thus may become uncomfortable or painful to the patient. As such, the amplitude of the alternating current that is delivered via the transducer arrays may be controlled so that skin temperature (as measured on the skin below the transducer arrays) does not exceed a safety threshold (e.g., 41 degrees Celsius, for example). The temperature measurements on the patient's skin are obtained using temperature sensors (e.g., thermistors) placed beneath some of the disks of the transducer arrays. For example, each array may include eight thermistors, with one thermistor positioned beneath a respective disk in the array.

The thermistors in each array are connected via long wires to an electronic device called the "cable box" where the temperature from all thermistors (e.g., four arrays×eight thermistors per array) is measured and analog-to-digital converted into digital values for each thermistor. These measurements are then transmitted from the cable box to the electric field generator via additional wire(s) that facilitate two-way digital serial communications between the cable box and the field generator. The controller in the field generator uses the temperature measurements to control the current to be delivered via each pair of arrays in order to maintain temperatures below, for example, 41 degrees Celsius on the patient's skin. The current itself is delivered to each array via an additional wire (i.e., one wire for each array) that runs from the field generator through the cable box to the array. However, attaching temperature sensors and transducer arrays to a patient is cumbersome with the amount of wires.

BRIEF SUMMARY OF THE INVENTION

In some embodiments, an apparatus for imposing electric fields through a target region in a body of a patient is described. The apparatus may comprise at least one transducer array, a sensor array, a circuit and a controller. The at least one transducer array has a plurality of electrode elements configured for placement on the body of the patient, the electrode elements configured to provide TTFields via an alternating current waveform. The sensor array has a plurality of temperature sensors positioned within proximity to the plurality of electrode elements, a plurality of first temperature sensors of the sensor array connected to a first conductor, and a plurality of second temperature sensors connected to a second conductor. The circuit is configured to provide a known amount of electricity via the first conductor and the second conductor to a third temperature sensor, the third temperature sensor within the first plurality of first temperature sensors, and within the second plurality of second temperature sensors, and obtain a first electrical reading corresponding to a first temperature reading of the third temperature sensor. The controller adjusts the alternating current waveform based on the first temperature reading.

DETAILED DESCRIPTION

Before explaining at least one embodiment of the inventive concept(s) in detail by way of exemplary language and results, it is to be understood that the inventive concept(s) is not limited in its application to the details of construction and the arrangement of the components set forth in the following description. The language used herein is intended to be given the broadest possible scope and meaning; and the embodiments are meant to be exemplary—not exhaustive.

Unless otherwise required by context, singular terms shall include pluralities and plural terms shall include the singular.

All patents, published patent applications, and non-patent publications referenced in any portion of this application are herein expressly incorporated by reference in their entirety to the same extent as if each individual patent or publication was specifically and individually indicated to be incorporated by reference. As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds. The term "plurality" refers to "two or more."

The use of the term "at least one" will be understood to include one as well as any quantity more than one. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment.

Throughout this application, the term "about" is used to indicate that a value includes the inherent variation of error for an apparatus/device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. For example, the term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The term "patient" as used herein includes human and veterinary subjects. "Mammal" for purposes of treatment refers to any animal classified as a mammal, including (but not limited to) humans, domestic and farm animals, nonhuman primates, and any other animal that has mammary tissue.

Circuitry, as used herein, may be analog and/or digital components, or one or more suitably programmed processors (e.g., microprocessors) and associated hardware and software, or hardwired logic. Also, "components" may perform one or more functions. The term "component," may include hardware, such as a processor (e.g., microprocessor), an application specific integrated circuit (ASIC), a field programmable gate array (FPGA), a combination of hardware and software, and/or the like. The term "processor" as used herein means a single processor or multiple processors working independently or together to collectively perform a task.

As discussed above, attaching temperature sensors and transducer arrays to a patient is cumbersome with the amount of wires. As such, the inventor has recognized a need for new and improved array assemblies that reduce the number of wires, which may increase patient comfort and reduce cost. It is to such assemblies and methods of producing and using the same, that the present disclosure is directed.

Turning now to the inventive concept(s), certain non-limiting embodiments thereof include an apparatus for imposing electric fields through a target region in a body of a patient is described. The apparatus may comprise at least one transducer array, a sensor array, a circuit and a controller. The at least one transducer array has a plurality of electrode elements configured for placement on the body of the patient, the electrode elements configured to provide TTFields via an alternating current waveform. The sensor array has a plurality of temperature sensors positioned within proximity to the plurality of electrode elements, a plurality of first temperature sensors of the sensor array connected to a first conductor, and a plurality of second temperature sensors connected to a second conductor. The circuit is configured to provide a known amount of electricity via the first conductor and the second conductor to a third temperature sensor, the third temperature sensor within the first plurality of first temperature sensors, and within the second plurality of second temperature sensors, and obtain a first electrical reading corresponding to a first temperature reading of the third temperature sensor. The controller adjusts the alternating current waveform based on the first temperature reading.

Figure 1:
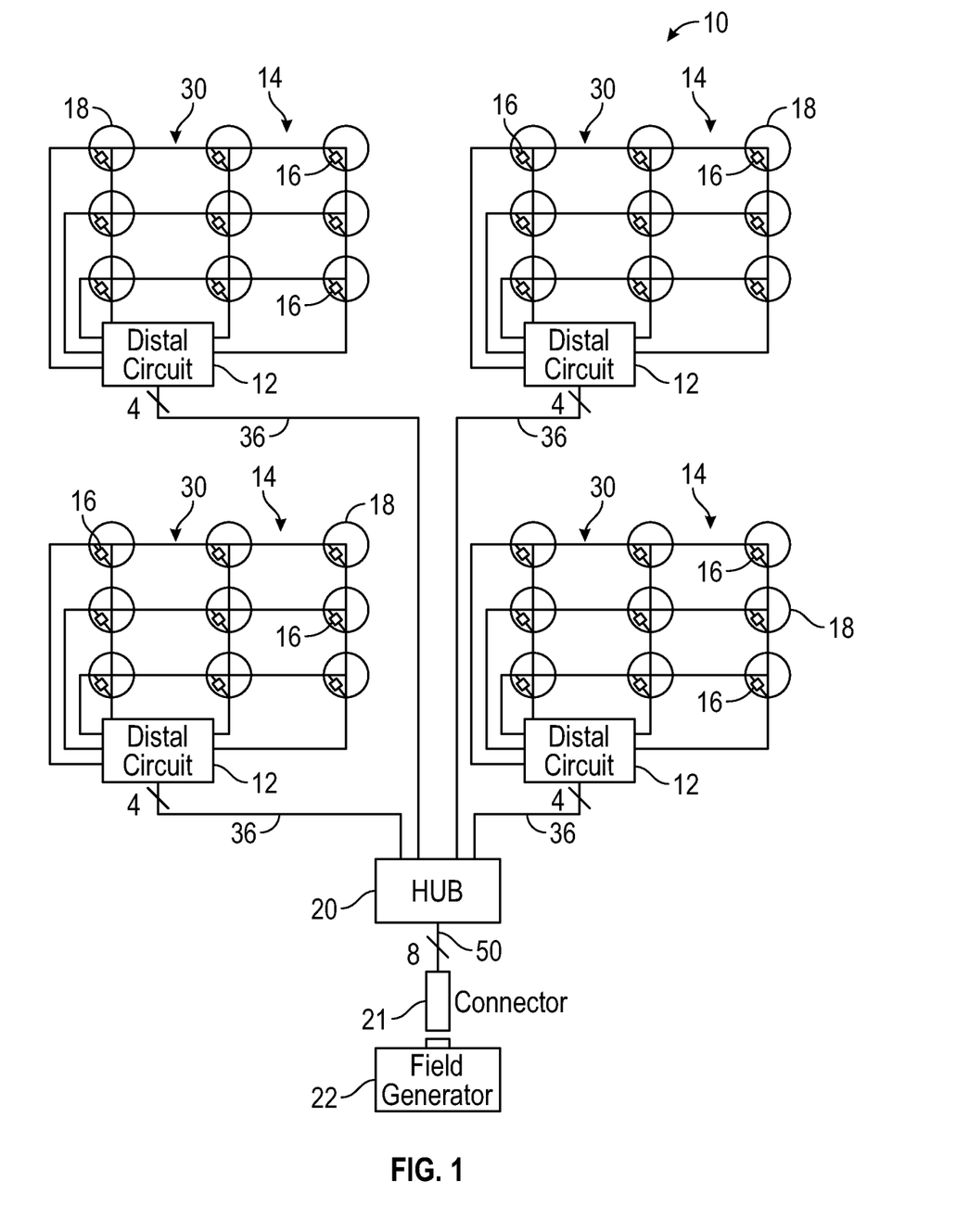
FIG. 1 is a block diagram of an exemplary system for measuring the temperature of transducer arrays applying TTFields to a body of a patient in accordance with the present disclosure.
Figure 2:
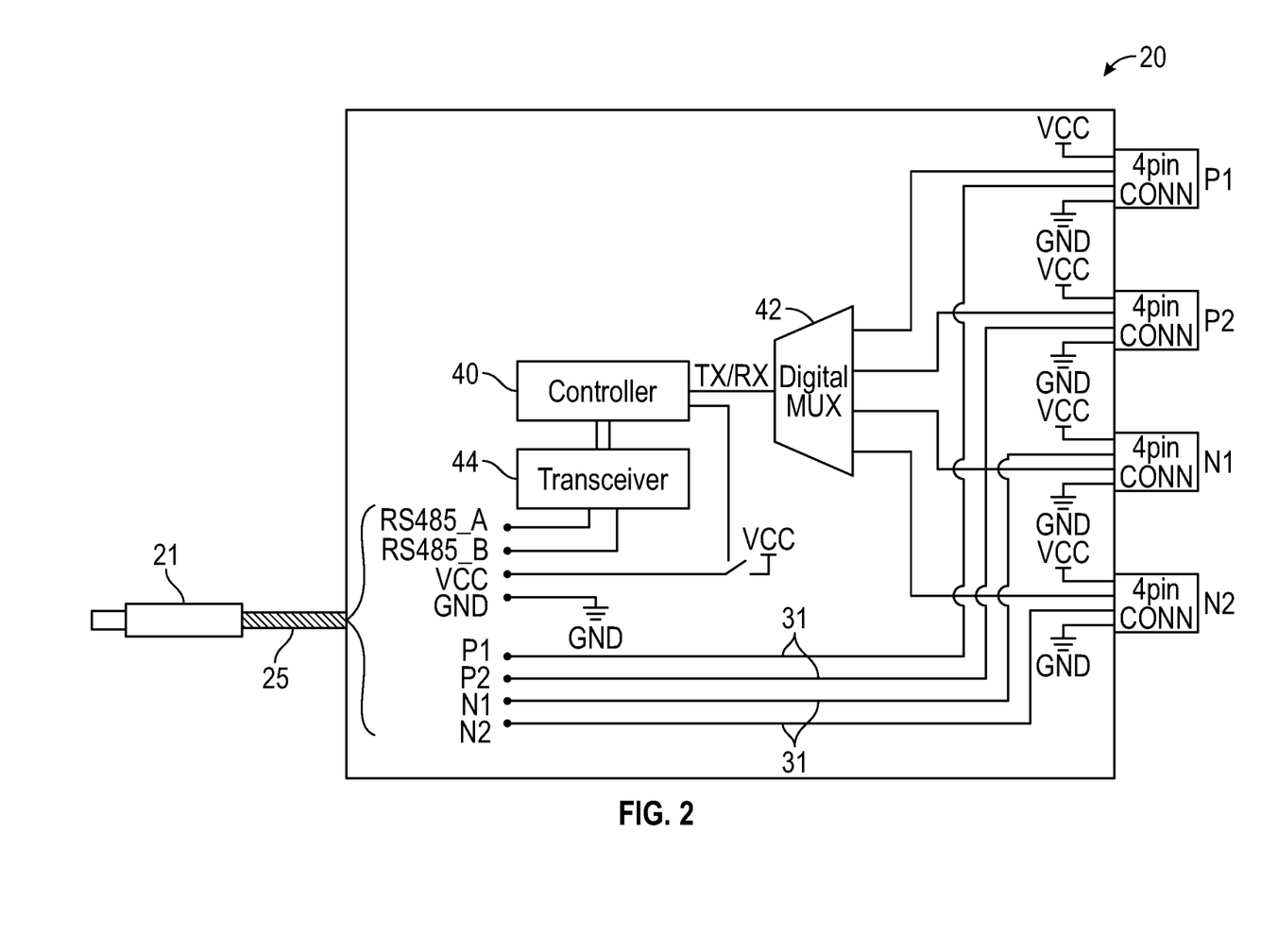
FIG. 2 is a schematic diagram of an exemplary hub for use in the system illustrated in FIG. 1 in accordance with the present disclosure.

Referring now to the drawings, and in particular FIGS. 1 and 2, shown therein are block diagrams of an exemplary embodiment of a system 10 having one or more circuit 12. The circuit 12 is described herein by way of example as one or more distal circuits 12 positioned in close proximity to one or more transducer arrays 14 to obtain one or more temperature readings from one or more temperature sensors 16. Each of the transducer arrays 14 includes one or more electrode elements 18. Alternative constructions for the transducer arrays 14 may also be used, including, for example, transducer arrays using ceramic elements that are not disc-shaped, and/or transducer arrays that use non-ceramic dielectric materials positioned over a plurality of flat conductors. Examples of the latter include polymer films disposed over pads on a printed circuit board or over flat pieces of metal. Transducer arrays that use electrode elements that are not capacitively coupled may also be used. In this situation, each element of the transducer array may be implemented using a region of a conductive material that is configured for placement against a person's body, with no insulating dielectric layer disposed between the conductive elements and the body. Examples of the conductive material include, but are not limited to, a conductive film, a conductive fabric, and/or a conductive foam. Other alternative constructions for implementing the transducer arrays may also be used, as long as they are (a) capable of delivering TTFields to the person's body and (b) utilize the improved connector designs described herein positioned in the locations specified herein. Optionally, a layer of hydrogel may be disposed between the transducer arrays and a body of a person in any of the embodiments described herein.

The one or more temperature sensors 16 are positioned to detect the temperature at the electrode elements 18. In some embodiments, the temperature sensors 16 may be thermistors, thermocouples, resistance temperature detectors (RTDs), integrated circuit temperature sensors such as the Analog Devices AD590 and the Texas Instruments LM135, and/or combinations thereof.

Each distal circuit 12 interfaces with the one or more temperature sensors 16 that are incorporated into the respective transducer array 14 to obtain temperature readings from each of the one or more temperature sensor 16. The distal circuit 12 then may convert (e.g., analog to digital) the temperature readings, forward the temperature reading and/or send the temperature readings to a hub 20. The hub 20 may then forward the temperature reading and/or send the temperature readings to a field generator 22 (e.g., via a serial communication link). In some embodiments, the field generator 22 may determine, based on the temperature readings, adjustment of the current to the transducer arrays 14.

In some embodiments, conductors 30 may extend distally beyond the distal circuit 12 into the transducer array 14. Each temperature sensor 16 may be connected to at least two conductors 30 such that selective activation of the at least two conductors 30 may activate the temperature sensor 16 to obtain one or more temperature readings (e.g., selective activation on a time basis).

Additionally, wiring extending from the distal circuit 12 may include but is not limited to, one or more conductors for the one or more temperature sensors' common ground, and one or more conductors for the TTFields signal (i.e., the AC current for the electrode elements), and the like. In some embodiments, the distal circuit 12 may be implemented using a single-chip microcontroller or Programmable System on Chip (PSoC) with a built in analog front end and multiplexer. Suitable part numbers for this purpose include the CY8C4124LQI-443, manufactured by Cypress Semiconductor Corp., having a principle place of business in San Jose, California.

As one skilled in the art will appreciate, some embodiments may include one or more microcontrollers having built-in and/or discrete analog front ends and/or multiplexers. For example, the analog front end and multiplexer may obtain temperature readings from the one or more temperature sensors 16. Those temperature readings may then be digitized and/or transmitted to the hub 20, (e.g., via serial data link). In some embodiments, each distal circuit 12 may also include one or more pass-through conductors 34 (see FIG. 3). The one or more pass-through conductors 34 may be configured to route one or more TTFields signal that originated in the field generator 22 to the transducer array 14.

In some embodiments, each distal circuit 12 may be connected to the hub 20 via one or more cable 36. Conductors 34 in each cable 36 may run between the distal circuit 12 and the hub 20. For example, in FIG. 3, four conductors 34 run between each distal circuit 12 and the hub 20, including, one conductor 34 for power ($V_{CC}$), one conductor 34 for grounding (GND), one conductor for serial data communication (DATA), and one for the TTF signal.

Generally, the hub 20 may receive one or more temperature readings from each of the distal circuits 12 and may send the one or more temperature readings to the field generator 22. Any of a wide variety of architectures may be used to receive and send the one or more temperature readings. For example, FIG. 2 illustrates a controller 40 configured to send a signal to a digital multiplexer (Digital MUX) 42 that commands the digital multiplexer 42 to select one of the distal circuits 12 such that the hub 20 may receive digital data from the distal circuit 12 (e.g., the first distal circuit 12).

The controller 40 receives the one or more temperature readings from the selected input of the distal circuit 12 and transmits the one or more temperature readings to the field generator 22 via the transceiver 44. The controller 40 may then update the control signal to the digital multiplexer 42 such that the digital multiplexer 42 selects another distal circuit 12 (e.g., the second distal circuit 12). The controller 40 then receives one or more temperature readings from the input of the second distal circuit 12 and transmits one or more temperature readings to the field generator 22. Corresponding sequences may be then performed to obtain suitable temperature readings (e.g., nine temperature readings) from each of the distal circuits 12. In some embodiments, the entire sequence of obtaining each of the one or more temperature readings from each of the distal circuits 12 or a portion of the sequence may be repeated periodically (e.g., every 1/100 second, 1 second, 10 seconds, or 30 seconds, etc.) to update the one or more temperature readings that are provided to the field generator 22.

In some embodiments, the controller 40, the digital multiplexer 42, and/or the transceiver 44 may be integrated together into a single chip. In some embodiments, the controller 40 and the digital multiplexer 42 may be integrated together into circuitry including a single chip, and a separate transceiver 44 is used. For example, the controller 40 and the digital multiplexer 42 may be implemented using a Cypress CY8C4244LQI-443, manufactured by Cypress Semiconductor Corp., having a principle place of business in San Jose, California, and the transceiver 44 may be implemented using a Linear Technology LTC2856CMS8-2 #PBF, manufactured by Linear Technology Corp., having a principle place of business in Milpitas, California. The controller 40 and/or the digital multiplexer 42 may be implemented as a processor executing software to perform the functions described herein.

The hub 20 may communicate with the field generator 22 using any conventional communication technique (e.g., RS485). In some embodiments, the hub 20 may include one or more pass-through conductors configured to pass one or more TTField signals directly from the field generator 22 to each of the transducer arrays 14. In some embodiments, the hub 20 may communicate with the field generator 22 via an 8-conductor spiral cable 50, optionally connecting via a connector 21 (FIG. 1). For example, the hub 20 may communicate with the field generator 22 via an 8-conductor spiral cable 25 wherein four wires (e.g. P1, P2, N1, N2) may provide for TTFields signals from each transducer array 14, one wire may provide for ground (GND), one wire may provide for voltage ($V_{CC}$) to the distal circuits 12, and two wires may provide for communication (RS485A and RS485B). It should be noted that use of 8-conductor spiral cable 50 is configured to be backwards compatible with prior versions of TTField delivery systems within the art as one skilled in the art will appreciate.

Communication wires may be configured to implement data communications between the distal circuit 12, the hub 20 and the field generator 22 (i.e., for the temperature data). In some embodiments, one wire may be configured to implement communication in each direction. In some embodiments, wire count between the hub 20 and the field generator 22 can be reduced by replacing multiple data communication wires with a single data wire that implements two-way communication (using a conventional single wire communication protocol).

Figure 3:
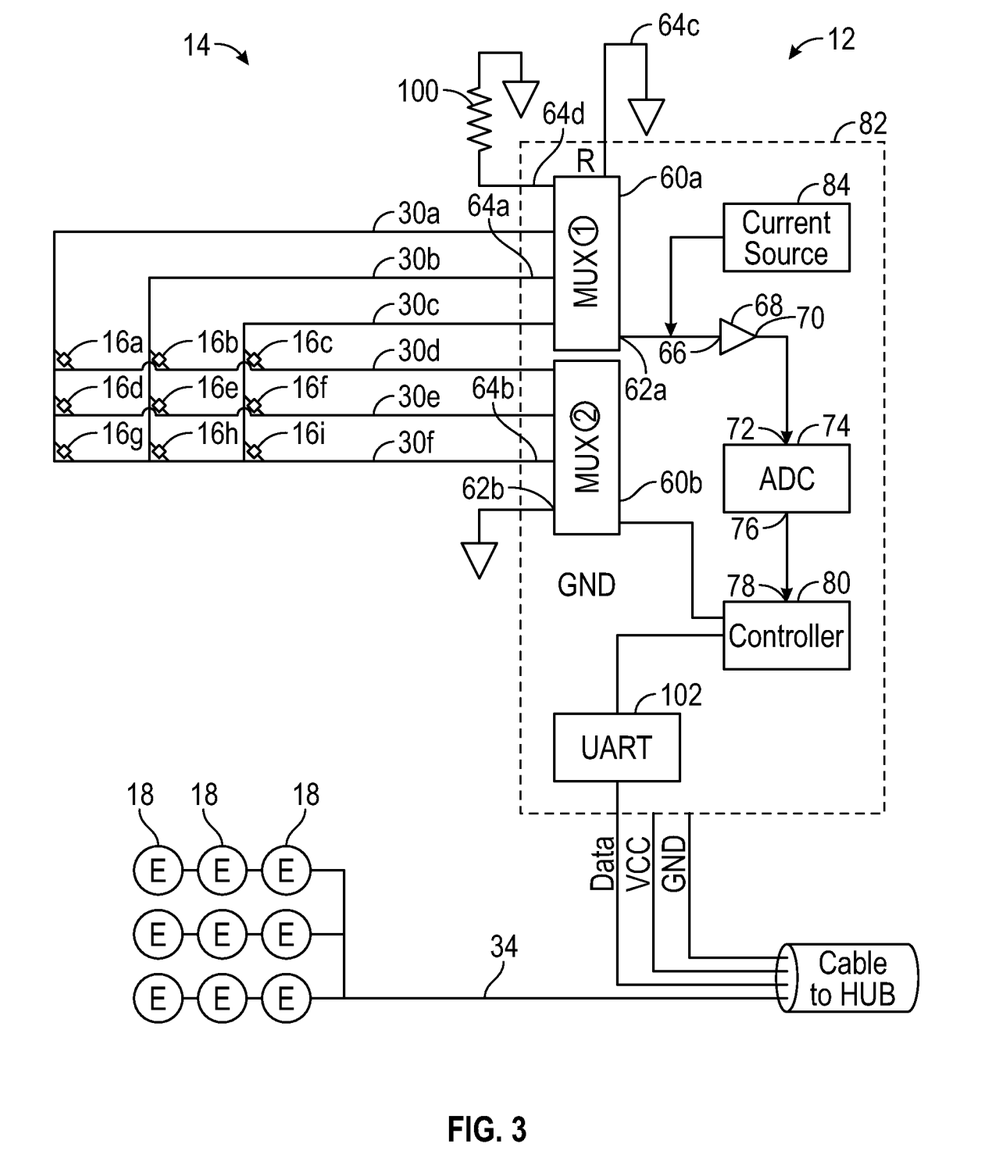
FIG. 3 is a schematic diagram of an exemplary distal circuit for use in the system illustrated in FIG. 1 in accordance with the present disclosure.

FIG. 3 is a schematic diagram of an exemplary distal circuit 12 for interfacing the hub 20 with the one or more transducer array 14. Each transducer array 14 may include one or more electrode elements 18 and one or more temperature sensors 16 (e.g. 16a-i in FIG. 3) positioned to sense temperatures of the one or more electrode elements 18. The one or more temperature sensors 16 may include, but are not limited to, thermistors, thermocouples, RTDs, integrated circuit temperature sensors such as the Analog Devices AD590 and the Texas Instruments LM135, and/or combinations thereof. It is contemplated that any temperature sensor 16 known within the art may be used if configured to provide an accurate and/or precise temperature reading in accordance with the present disclosure. In some embodiments, one or more temperature sensors 16 may be thermistors.

The distal circuit 12 may include a first multiplexer (MUX 1) 60a and a second multiplexer (MUX 2) 60b. Generally, the first multiplexer 60a drives a known amount of electricity (e.g., current) to the one or more temperature sensor 16 and the second multiplexer 60b electrically connects one or more temperature sensor 16 to a reference point (e.g., GND).

The first multiplexer 60a includes an output 62a and one or more selectable inputs 64a. Each of the one or more selectable inputs 64a may be connected to two or more temperature sensors 16. Similarly, the second multiplexer 60b includes an output 62b and one or more selectable inputs 64b. Each of the one or more selectable inputs 64b may be connected to two or more temperature sensors 16. To that end, each temperature sensor 16 may be connected to at least two conductors 30. At least one terminal 64c may be a common ground. In some embodiments, the output 62a of the first multiplexer 60a may be provided to an input 66 of an amplifier 68, (e.g., amplifier having a high input impedance such as an op amp configured as a voltage follower). Output 70 of the amplifier 68 may be provided to an input 72 of an analog to digital converter (ADC) 74. Output 76 of the analog to digital converter is provided to input 78 of a controller 80. The controller 80 may include circuitry including but not limited to a processor executing computer executable instructions, e.g., software, to perform the functions described herein.

In some embodiments, the controller 80 may be configured to orchestrate operation of one or more of the components within the dashed line 82. The controller 80 may be configured to send one or more commands to the first multiplexer 60a and second multiplexer 60b to select two or more conductors 30 in communication with one of the temperature sensors 16, in order to obtain a temperature reading from that temperature sensor 16. In some embodiments, the first multiplexer 60a and 60b are configured to provide an open circuit with respect to the unselected conductors 30 so that only a particular one of the temperature sensors 16 is read at any particular instant of time.

In some embodiments, temperature readings may be obtained by routing a known amount of electricity, e.g., current, through the at least two conductors 30 to the temperature sensor 16 (e.g., thermistor) and measuring an electrical reading, e.g., voltage, that appears across the temperature sensor 16. For example, a programmable current source 84 may be configured to generate a known current (e.g., 150 μA) through the at least two conductors 30. The first multiplexer 60a may be bidirectional such that the known current may be routed to the temperature sensor 16 via the selected conductors 30 by the first multiplexer 60a.

Figure 4A:
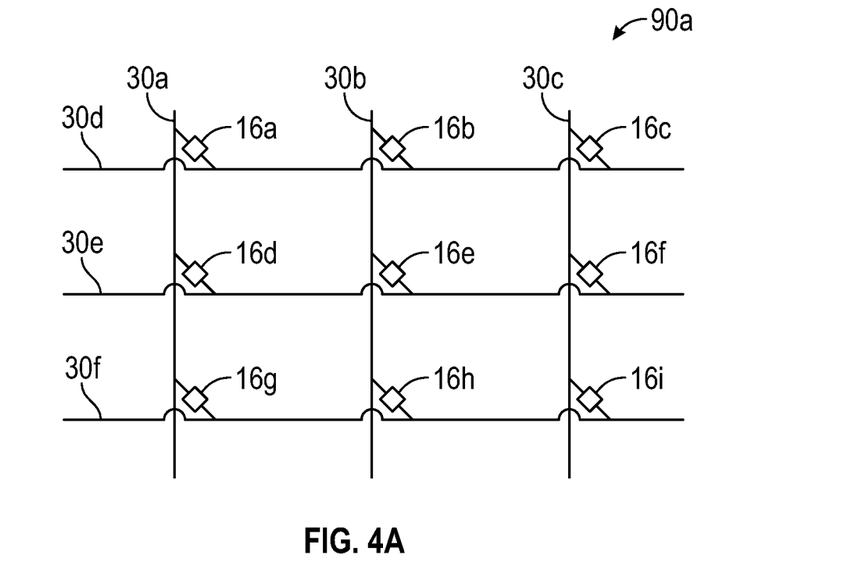
FIGS. 4A-4C illustrate schematic diagrams of exemplary embodiments of sensor arrays for use in the system illustrated in FIG. 1 in accordance with the present disclosure.

Referring to FIGS. 3 and 4A, temperature readings obtained from temperature sensors 16 within a sensor array 90a may be obtained using selective activation of at least two conductors 30. A plurality of first temperature sensors 16a, 16d, and 16g, for example, of the sensor array 90a are connected to a first conductor 30a. A plurality of second temperature sensors 16a, 16b and 16c, for example, of the sensor array 90a are connected to a second conductor 30d. The controller 80 sends one or more commands to the first multiplexer 60a and the second multiplexer 60b to select at least two conductors 30a and 30d in communication with a third temperature sensor 16a (which may also be referred to herein as a second temperature sensor) within the sensor array 90a, and configures the current source 84 to generate a known current via the two conductors 30a and 30d. In this example, the third temperature sensor 16a is within the plurality of first temperature sensors (16a, 16d and 16g) and also within the plurality of second temperature sensors (16a, 16b, and 16c).

The known current from the current source 84 is configured to flow through the first multiplexer 60a to the third temperature sensor 16a via the two conductors 30a and 30d connected to the third temperature sensor 16a resulting in a voltage appearing across the third temperature sensor 16a and at the output 62a of the first multiplexer 60a. In some embodiments, the known current from the current source 84 is configured to flow through the first multiplexer 60a to the third temperature sensor 16a via the two conductors 30a and 30d connected to the third temperature sensor 16a resulting in a voltage appearing across the third temperature sensor 16a and the output 62a of the first multiplexer 60a. The input 66 of the amplifier 68 receives the voltage appearing across the third temperature sensor 16a, the amplifier 68 amplifies the voltage, and then provides the amplified voltage to the input 72 of the analog to digital converter 74. The controller 80 instructs the analog to digital converter 74 to digitize the resulting voltage. The controller 80 obtains the digitized resulting voltage reading from the analog to digital converter 74 and temporarily stores the digitized resulting voltage reading (which corresponds to the third temperature sensor 16a) in a buffer and the digitized resulting voltage reading is used to determine a temperature reading based on the digitized resulting voltage reading. The digitized resulting voltage reading may be referred to herein as a first electrical reading. The procedure may be repeated, sequentially, for each of the temperature sensors 16 (i.e. 16a-i) with conductors 30 (i.e. 30a-f) within the sensor array 90a. For example, to obtain a reading from the temperature sensor 16b, the controller 80 sends one or more commands to the first multiplexer 60a and the second multiplexer 60b to select the at least two conductors 30b and 30d both of which are in communication with the temperature sensor 16b, and configures the current source 84 to generate a known current to the at least two conductors 30b and 30d. The known current from the current source 84 is configured to flow through the first multiplexer 60a into the temperature sensor 16b via the conductor 30b and to the second multiplexer 60b via the conductor 30d resulting in a voltage appearing across that temperature sensor 16b and at the output 62a of the first multiplexer 60a. The input 66 of the amplifier 68 receives the voltage appearing across the temperature sensor 16b, the amplifier 68 amplifies the voltage, and then provides the amplified voltage to the input 72 of the analog to digital converter 74. The controller 80 instructs the analog to digital converter 74 to digitize the resulting voltage. The controller 80 obtains the digitized resulting voltage reading from the analog to digital converter 74 and temporarily stores the digitized resulting voltage reading (which corresponds to the third temperature sensor 16a) in a buffer and the digitized resulting voltage reading is used to determine a temperature reading based on the digitized resulting voltage reading. The digitized resulting voltage reading from the temperature sensor 16b may be referred to herein as a second electrical reading. Similarly, to obtain a reading from the temperature sensor 16h, the controller 80 sends one or more commands to the first multiplexer 60a and the second multiplexer 60b to select the at least two conductors 30b and 30f in communication with the temperature sensor 16h, and configures the current source 84 to generate a known current. The known current from the current source 84 is configured to flow through the first multiplexer 60a into the temperature sensor 16h via the conductor 30b and to the second multiplexer 60b via the conductor 30f resulting in a voltage appearing across that temperature sensor 16h and at the output 62a of the multiplexer 60a. The controller 80 may pass the first temperature reading and/or the second temperature reading to the controller 40 within the hub 20, and the controller 40 may communicate with the field generator 22 to adjust the alternating current waveform based on the first temperature reading and/or the second temperature reading.

Figure 4B:
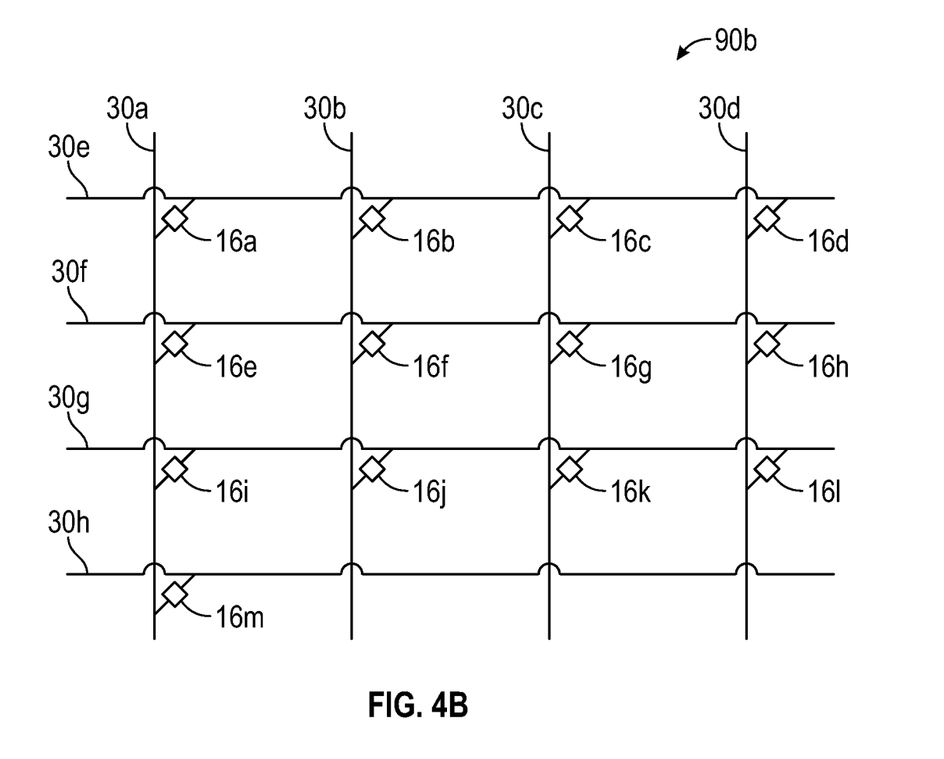
Figure 4C:
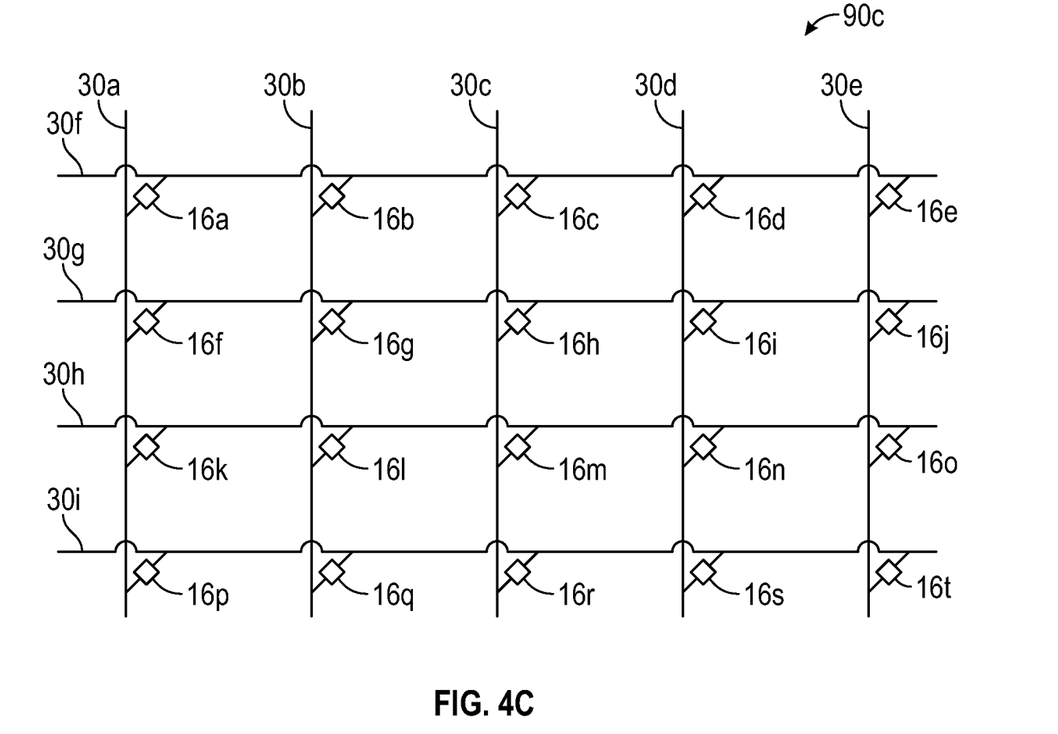

It should be understood that additional conductors 30 may be used to increase the number of temperature sensors 16 within the sensor array 90. For example, FIG. 4B illustrates another exemplary embodiment of a sensor array 90b having thirteen temperature sensors 16a-16m connected to conductors 30a-30h. Selective activation of at least two predetermined conductors 30 may result in a voltage appearing across at least one temperature sensor 16 connected to the at least two conductors 30 resulting in the temperature reading as described herein. FIG. 4C illustrates another exemplary embodiment of a sensor array 90c having twenty temperature sensors 16a-16t connected to conductors 30a-30i. Selective activation of at least two conductors 30 may result in a voltage appearing across the temperature sensor 16 connected to the at least two conductors 30 resulting in the temperature reading as described herein.

Figure 5:
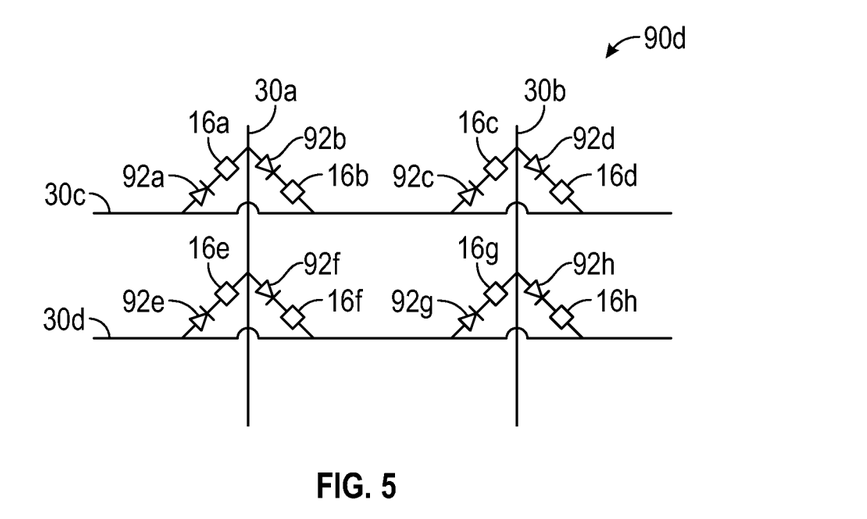
FIG. 5 is a schematic diagram of another exemplary embodiment of a sensor array for use in the system illustrated in FIG. 1 in accordance with the present disclosure.

FIG. 5 illustrates another exemplary embodiment of a sensor array 90d that includes a reduced number of conductors 30 (30a-d) relative to the embodiments of FIG. 4A-4C including a plurality of electronic switches 92 (92a-h), such as diodes configured to provide selective activation of one temperature sensor 16 (FIG. 5 shows 16a-h) when more than one temperature sensor 16 are connected to two conductors 30. In one embodiment, the selection of the temperature sensor 16 can be accomplished by providing a particular polarity of voltage across the two conductors 30. Generally, by providing a positive polarity or a negative polarity to a combination of conductors 30, particular temperature sensors 16 may be activated. For example, two temperature sensors 16g and 16h are connected in circuit with the two conductors 30b and 30d, and two electronic switches 92g and 92h. The electronic switch 92g is in series with the temperature sensor 16g; and the electronic switch 92h is in series with the temperature sensor 16h. The electronic switch 92g is configured to conduct based upon a negative polarity, and the electronic switch 92h is configured to conduct based upon a positive polarity. By applying a positive polarity across conductors 30b and 30d, temperature sensor 16h may be activated (and temperature sensor 16g is not activated) providing a temperature reading. By applying a negative polarity across the same conductors 30b and 30d, temperature sensor 16g may be activated (and temperature sensor 16h not activated) providing a temperature reading.

Referring to FIG. 3, in some embodiments, a conventional voltage divider approach for interfacing with the one or more temperature sensors 16 may be used. In some embodiments, additional readings may be obtained and used for self-calibration to increase the accuracy and/or precision of the temperature readings obtained from the one or more temperature sensors 16. For example, in FIG. 3, at least one input 64c of the first multiplexer 60a is connected to ground, and at least one input 64d of the first multiplexer 60a is connected to a precision resistor 100. The controller 80 may temporarily store the digitized readings from the precision resistor 100 and the grounded input 64c in a buffer and/or any memory configured to store data. These additional readings may ultimately be used to calibrate the readings that were obtained from the one or more temperature sensors 16. In some embodiments, such calibration may be implemented via the controller 80. In some embodiments, calibration may occur prior to transmission of the digital data that corresponds to the temperature readings. In some embodiments, calibration may be implemented in a downstream processor (e.g., the controller 40 in the hub 20) such that the digital data corresponding to the precision resistor 100 (and optionally the grounded input 64) may be transmitted to a downstream processor, in addition to, any uncalibrated temperature readings obtained from the one or more temperature sensor 16.

In some embodiments, calibration using the precision resistor 100 may compare the actual voltage measured across the precision resistor 100 with an expected voltage based on Ohm's law, the known value of the precision resistor 100, and the expected value of the current being produced by the current source 84. Deviations between the actual measured voltage and the expected voltage may be used to determine subsequent measurements (e.g., use as a multiplier) from the one or more temperature sensors 16.

In some embodiments, the controller 80 in the distal circuit 12 may be configured to communicate with the hub 20 via universal asynchronous receiver-transmitter (UART) 102, and transmit the temperature readings obtained from the one or more temperature sensors 16 to the hub 20. In some embodiments, the controller 80 may be a processor programmed to operate autonomously and configured to automatically collect temperature readings from each of the one or more temperature sensors 16, storing the result in a buffer as described above, and subsequently transmitting contents of the buffer (i.e., readings for each of the temperature sensors 16, and optionally the additional readings described herein) to the hub 20.

In some embodiments, the controller 80 may be a processor programmed to operate as a slave to a master controller located in the hub 20. For example, the controller 80 may begin in a quiescent state, wherein the controller 80 solely monitors incoming commands from the master controller that arrive via the UART 102. Examples of commands that can arrive from the master controller may include, but are not limited to, "collect samples" command, "send data" command, and/or the like. When the controller 80 recognizes that a "collect samples" command has arrived, the controller 80 may be configured to initiate the method described herein to obtain one or more temperature readings from the one or more temperature sensors 16, and store results in the buffer and/or any memory configured to store data. In another example, the controller 80 may recognize a "send data" command, and execute a method to transmit previously collected temperature readings from the buffer and/or memory to the hub 20 via the UART 102.

In some embodiments, temperature measurements may be synchronized. For example, the controller 40 in the hub 20 may send a "collect samples" command to one or more controllers 80 in the distal circuit 12 either simultaneously or in rapid succession, such that the temperature readings obtained from each of the transducer arrays 14 may be obtained at or near the same time. In some embodiments, the temperature readings may be collected by the hub 20 in one or more batches of each controller 80.

Most systems that use TTFields to treat tumors switch the direction of the field that is being applied to the tumor periodically (e.g. every second). To minimize noise in the temperature measurements, a small time gap during which the field is not applied in either direction may be introduced, and the temperature measurements can be made during the time gap. In some embodiments, the controller 40 located in the hub 20 may synchronize timing of the "collect samples" command to all controllers 80 such that each of the distal circuits 12 may obtain temperature readings during the time gap. The temperature readings simultaneously obtained from each transducer array 14 may minimize duration of the time gap. For example, if the system 10 requires 100 μs to obtain a single measurement, taking thirty-six measurements in sequence (i.e., four distal circuits×nine temperature sensors 16 at each distal circuit 12, for example) may take 3.6 ms. In contrast, if each of four distal circuits 12 operates in parallel, each distal circuit 12 can obtain 9 samples in 900 μs, such that 36 samples can be obtained in 900 μs. It should be noted that the "send data" command may not be sensitive to noise such that the "send data" command can be executed while the fields remain on, and as such, is not time-critical.

In some embodiments, some or all of the following components may be implemented by a single integrated circuit: first multiplexer 60a, second multiplexer 60b, amplifier 68, analog to digital converter 74, controller 80, UART 102, and current source 84. One example of a single integrated circuit that includes all of these functional blocks is the Cypress CY8C4124LQI-443T programmable system on chip (PSoC), manufactured by Cypress Semiconductor Corp., having a principal place of business in San Jose, California.

Embodiments illustrated under any heading or in any portion of the disclosure may be combined with embodiments illustrated under the same or any other heading or other portion of the disclosure. Any combination of the elements described herein in all possible variations thereof is encompassed by the invention unless otherwise indicated herein or otherwise clearly contradicted by context.

The invention includes other illustrative embodiments, such as the following:

Illustrative embodiment 1. An apparatus for imposing electric fields through a target region in a body of a patient, the apparatus comprising:

at least one transducer array having a plurality of electrode elements configured for placement on the body of the patient, the electrode elements configured to provide TTFields via an alternating current waveform;

a sensor array having a plurality of temperature sensors positioned within proximity to the plurality of electrode elements, a plurality of first temperature sensors of the sensor array connected to a first conductor, and a plurality of second temperature sensors connected to a second conductor;

a circuit configured to provide a known amount of electricity via the first conductor and the second conductor to a third temperature sensor, the third temperature sensor within the first plurality of first temperature sensors, and within the second plurality of second temperature sensors, and obtain a first electrical reading corresponding to a first temperature reading of the third temperature sensor; and a controller adjusting the alternating current waveform based on the first temperature reading.

Illustrative embodiment 2. The apparatus of claim 1, wherein the circuit further comprises:

a current source providing the known amount of electricity;

a first multiplexer having an input and an output, the first multiplexer connected to the current source;

a second multiplexer having an input and an output, the second multiplexer connected to a reference point; and, a controller configured to send at least one command to the first multiplexer to select the first conductor and at least one command to the second multiplexer to select the second conductor.

Illustrative embodiment 3. The apparatus of illustrative embodiment 2, wherein the controller is in communication with the current source and is configured to command the current source to generate the known amount of electricity to the first conductor and the second conductor.

Illustrative embodiment 4. The apparatus of illustrative embodiment 2, wherein the first electrical reading is obtained at the output of the first multiplexer.

Illustrative embodiment 5. The apparatus of illustrative embodiment 4, wherein the circuit further comprises an analog to digital converter configured to obtain the first electrical reading and provide a digitized resulting reading corresponding to the first temperature reading of the third temperature sensor.

Illustrative embodiment 6. The apparatus of illustrative embodiment 5, wherein the circuit further comprises a buffer configured to store the digitized resulting reading of the third temperature sensor.

Illustrative embodiment 7. The apparatus of illustrative embodiment 5, wherein the circuit further comprises an amplifier configured to receive the first electrical reading and provide an amplified voltage to the analog to digital converter.

Illustrative embodiment 8. The apparatus of illustrative embodiment 1, wherein the known amount of electricity is a known current, and wherein the sensor array includes at least twelve temperature sensors, with each temperature sensor connected to at least two conductors such that providing the known current to the at least two conductors connected to the temperature sensor provides a voltage across the temperature sensor.

Illustrative embodiment 9. The apparatus of illustrative embodiment 1, wherein the known amount of electricity is a known current, and wherein the sensor array includes at least thirteen temperature sensors, with each temperature sensor connected to two conductors such that providing current to the two conductors connected to the temperature sensor provides a voltage across the temperature sensor.

Illustrative embodiment 10. The apparatus of illustrative embodiment 1, wherein the sensor array includes at least twenty-four temperature sensors, with each temperature sensor connected to two conductors such that providing the known amount of electricity to the two conductors connected to the temperature sensor provides an electrical reading across the temperature sensor.

Illustrative embodiment 11. The apparatus of illustrative embodiment 1, wherein the sensor array includes a plurality of electronic switches configured to provide selective activation of the third temperature sensor.

Illustrative embodiment 12. The apparatus of illustrative embodiment 11, wherein a first electronic switch is positioned in series with the third temperature sensor, the first electronic switch being configured to conduct upon a first predetermined polarity being placed across the first electronic switch.

Illustrative embodiment 13. The apparatus of illustrative embodiment 12, wherein a second electronic switch is positioned in series with a fourth temperature sensor such that negative polarity across the first conductor results in a voltage across the fourth temperature sensor, the second electronic switch being configured to conduct upon a second predetermined polarity being placed across the second electronic switch.

Illustrative embodiment 14. An apparatus for imposing electric fields through a target region in a body of a patient, the apparatus comprising:
at least one transducer array having a plurality of electrode elements configured for placement on the body of the patient, the electrode elements configured to provide TTFields via an alternating current waveform;
a sensor array having a first temperature sensor and a second temperature sensor, the first temperature sensor of the sensor array connected to a first conductor and a second conductor, the second temperature sensor connected to the first conductor and a third conductor; and,
a controller configured to:
provide a first known amount of electricity for activation of the first temperature sensor via the first conductor and the second conductor and to provide a second known amount of electricity for activation of the second temperature sensor via the first conductor and the third conductor;
obtain a first electrical reading induced by the first known amount of electricity and a second electrical reading induced by the second known amount of electricity; and,
determine a first temperature reading based on the first electrical reading and a second temperature reading based on the second electrical reading; and
wherein the alternating current waveform is adjusted based on the first temperature reading and the second temperature reading.

Illustrative embodiment 15. The apparatus of illustrative embodiment 14, wherein the sensor array further comprises a first electronic switch in circuit with the first temperature sensor, and a second electronic switch in circuit with the second temperature sensor.

Illustrative embodiment 16. The apparatus of illustrative embodiment 15, wherein the controller is further configured to provide selective activation of the first electronic switch or the second electronic switch.

Illustrative embodiment 17. The apparatus of illustrative embodiment 16, wherein the first electronic switch is positioned in series with the first temperature sensor.

Illustrative embodiment 18. The apparatus of illustrative embodiment 16, wherein the second electronic switch is positioned in series with the second temperature sensor.

Illustrative embodiment 19. A method, comprising:
providing a first known amount of electricity via a first conductor and a second conductor to activate a first temperature sensor of a sensor array, the sensor array positioned in proximity to a transducer array having a plurality of electrode elements configured for placement on a body of a patient, the electrode elements configured to provide TTFields via an alternating current waveform;
obtaining a first temperature reading induced by activation of the first temperature sensor;
providing a second known amount of electricity via the first conductor and a third conductor to activate of a second temperature sensor;
obtaining a second temperature reading induced by activation of the second temperature sensor; and,
adjusting the alternating current waveform based on at least one of the first temperature reading and the second temperature reading.

Illustrative embodiment 20. The method of illustrative embodiment 19, wherein the step of adjusting the alternating current waveform is based on the second temperature reading.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed and claimed herein.

What is claimed is:

1. An apparatus for imposing electric fields through a target region in a body of a patient, the apparatus comprising:
   at least one transducer array having a plurality of electrode elements configured for placement on the body of the patient, the electrode elements configured to provide TTFields via an alternating current waveform;
   a sensor array having a plurality of temperature sensors positioned within proximity to the plurality of electrode elements, a plurality of first temperature sensors of the sensor array connected to a first conductor, and a plurality of second temperature sensors connected to a second conductor;
   a circuit configured to provide a known amount of electricity via the first conductor and the second conductor to a third temperature sensor, the third temperature sensor within the plurality of first temperature sensors, and within the plurality of second temperature sensors, and obtain a first electrical reading corresponding to a first temperature reading of the third temperature sensor; and
   a controller adjusting the alternating current waveform based on the first temperature reading.

2. The apparatus of claim 1, wherein the circuit further comprises:
   a current source providing the known amount of electricity;
   a first multiplexer having an input and an output, the first multiplexer connected to the current source;
   a second multiplexer having an input and an output, the second multiplexer connected to a reference point; and,
   a controller configured to send at least one command to the first multiplexer to select the first conductor and at least one command to the second multiplexer to select the second conductor.

3. The apparatus of claim 2, wherein the controller is in communication with the current source and is configured to command the current source to generate the known amount of electricity to the first conductor and the second conductor.

4. The apparatus of claim 2, wherein the first electrical reading is obtained at the output of the first multiplexer.

5. The apparatus of claim 4, wherein the circuit further comprises an analog to digital converter configured to obtain the first electrical reading and provide a digitized resulting reading corresponding to the first temperature reading of the third temperature sensor.

6. The apparatus of claim 5, wherein the circuit further comprises a buffer configured to store the digitized resulting reading of the third temperature sensor.

7. The apparatus of claim 5, wherein the circuit further comprises an amplifier configured to receive the first electrical reading and provide an amplified voltage to the analog to digital converter.

8. The apparatus of claim 1, wherein the known amount of electricity is a known current, and wherein the sensor array includes at least twelve temperature sensors, with each temperature sensor connected to at least two conductors such that providing the known current to the at least two conductors connected to the temperature sensor provides a voltage across the temperature sensor.

9. The apparatus of claim 1, wherein the known amount of electricity is a known current, and wherein the sensor array includes at least thirteen temperature sensors, with each temperature sensor connected to two conductors such that providing current to the two conductors connected to the temperature sensor provides a voltage across the temperature sensor.

10. The apparatus of claim 1, wherein the sensor array includes at least twenty-four temperature sensors, with each temperature sensor connected to two conductors such that providing the known amount of electricity to the two conductors connected to the temperature sensor provides an electrical reading across the temperature sensor.

11. The apparatus of claim 1, wherein the sensor array includes a plurality of electronic switches configured to provide selective activation of the third temperature sensor.

12. The apparatus of claim 11, wherein a first electronic switch is positioned in series with the third temperature sensor, the first electronic switch being configured to conduct upon a first predetermined polarity being placed across the first electronic switch.

13. The apparatus of claim 12, wherein a second electronic switch is positioned in series with a fourth temperature sensor such that negative polarity across the first conductor results in a voltage across the fourth temperature sensor, the second electronic switch being configured to conduct upon a second predetermined polarity being placed across the second electronic switch.

14. An apparatus for imposing electric fields through a target region in a body of a patient, the apparatus comprising:
   at least one transducer array having a plurality of electrode elements configured for placement on the body of the patient, the electrode elements configured to provide TTFields via an alternating current waveform;
   a first conductor, a second conductor and a third conductor,
   a sensor array having a plurality of temperature sensors, the first conductor, the second conductor and the third conductor, the first conductor, second conductor and third conductor each connected to two or more of the plurality of temperature sensors, a first temperature of the sensor array connected to the first conductor and the second conductor, a second temperature sensor connected to the first conductor and the third conductor; and,
   a controller configured to:
      provide a first known amount of electricity for activation of the first temperature sensor via the first conductor and the second conductor and to provide a second known amount of electricity for activation of the second temperature sensor via the first conductor and the third conductor;
      obtain a first electrical reading induced by the first known amount of electricity and a second electrical reading induced by the second known amount of electricity; and,
      determine a first temperature reading based on the first electrical reading and a second temperature reading based on the second electrical reading; and
   wherein the alternating current waveform is adjusted based on the first temperature reading and the second temperature reading.

15. The apparatus of claim 14, wherein the sensor array further comprises a first electronic switch in circuit with the first temperature sensor, and a second electronic switch in circuit with the second temperature sensor.

16. The apparatus of claim 15, wherein the controller is further configured to provide selective activation of the first electronic switch or the second electronic switch.

17. The apparatus of claim 16, wherein the first electronic switch is positioned in series with the first temperature sensor.

18. The apparatus of claim 16, wherein the second electronic switch is positioned in series with the second temperature sensor.

19. A method, comprising:
- in a circuit having a first conductor, a second conductor and a third conductor, with each of the first conductor, the second conductor and the third conductor connected to two or more temperature sensors of a sensor array,
- providing a first known amount of electricity via the first conductor and the second conductor to activate a first temperature sensor of the sensor array, the sensor array positioned in proximity to a transducer array having a plurality of electrode elements configured for placement on a body of a patient, the electrode elements configured to provide TTFields via an alternating current waveform;
- obtaining a first temperature reading induced by activation of a first temperature sensor;
- providing a second known amount of electricity via the first conductor and the third conductor to activate a second temperature sensor;
- obtaining a second temperature reading induced by activation of the second temperature sensor; and,
- adjusting the alternating current waveform based on at least one of the first temperature reading and the second temperature reading.

20. The method of claim 19, wherein the step of adjusting the alternating current waveform is based on the second temperature reading.

* * * * *

UNITED STATES PATENT AND TRADEMARK OFFICE
CERTIFICATE OF CORRECTION

| | | |
|---|---|---|
| PATENT NO. | : 11,883,652 B2 | Page 1 of 1 |
| APPLICATION NO. | : 17/550423 | |
| DATED | : January 30, 2024 | |
| INVENTOR(S) | : Yoram Wasserman | |

It is certified that error appears in the above-identified patent and that said Letters Patent is hereby corrected as shown below:

In the Specification

Column 2, Line 4: After "of electrodes" delete "fora" and replace with -- for a --.

Signed and Sealed this
Twenty-sixth Day of March, 2024

Katherine Kelly Vidal
*Director of the United States Patent and Trademark Office*